United States Patent
Yamaguchi et al.

(10) Patent No.: US 7,339,677 B2
(45) Date of Patent: *Mar. 4, 2008

(54) MICROCHEMICAL SYSTEM, AND PHOTOTHERMAL CONVERSION SPECTROSCOPIC ANALYSIS METHOD

(75) Inventors: Jun Yamaguchi, Tokyo (JP); Akihiko Hattori, Osaka (JP)

(73) Assignee: Nippon Sheet Glass Co., Ltd., Osaka (JP)

( * ) Notice: Subject to any disclaimer, the term of this patent is extended or adjusted under 35 U.S.C. 154(b) by 593 days.

This patent is subject to a terminal disclaimer.

(21) Appl. No.: 10/830,284

(22) Filed: Apr. 21, 2004

(65) Prior Publication Data

US 2004/0196466 A1    Oct. 7, 2004

Related U.S. Application Data (63) Continuation of application No. PCT/JP02/09464, filed on Sep. 13, 2002.

(30) Foreign Application Priority Data

Oct. 22, 2001    (JP) .............................. 2001-323350

(51) Int. Cl.
*G01N 21/00*    (2006.01)
(52) U.S. Cl. ..................................... 356/432
(58) Field of Classification Search ............... None
See application file for complete search history.

(56) References Cited

U.S. PATENT DOCUMENTS

| | | | |
|---|---|---|---|
| 4,927,268 A | 5/1990 | Carr et al. | |
| 4,938,593 A | 7/1990 | Morris et al. | |
| 5,513,006 A | 4/1996 | Schulz et al. | |
| 6,452,710 B1 | 9/2002 | Hiraga et al. | |
| 6,930,778 B2 * | 8/2005 | Yamaguchi et al. | ........ 356/432 |

(Continued)

FOREIGN PATENT DOCUMENTS

EP    1 087 223 A1    3/2001

(Continued)

OTHER PUBLICATIONS

English machine translation of Japanese Patent Application Publication No. 2001-59829.*

(Continued)

*Primary Examiner*—Gregory J. Toatley, Jr.
*Assistant Examiner*—Juan D. Valentin, II
(74) *Attorney, Agent, or Firm*—Frishauf, Holtz, Goodman & Chick, P.C.

(57) ABSTRACT

A microchemical system according to which measurement can be carried out with high sensitivity. The microchemical system 1 has a two-wavelength multiplexing device in which gradient index rod lenses 501 and 502 are connected together at an end face of each thereof and a dielectric multi-layer film filter 503 is formed between these end faces. Exciting light and detecting light is multiplexed by the two-wavelength multiplexing device, and then the exciting light and the detecting light are guided to an optical fiber unit 10 through an optical fiber 101 with a single mode. The optical fiber unit 10 has built therein a gradient index rod lens 102 at a leading end thereof, and the exciting light and the detecting light are irradiated onto a sample from the gradient index rod lens 102.

10 Claims, 6 Drawing Sheets

U.S. PATENT DOCUMENTS

| | | | |
|---|---|---|---|
| 6,941,041 B2 * | 9/2005 | Yamaguchi et al. | 385/34 |
| 7,092,099 B2 * | 8/2006 | Yamaguchi et al. | 356/432 |
| 7,142,305 B2 * | 11/2006 | Yamaguchi et al. | 356/432 |
| 2003/0002038 A1 | 1/2003 | Mawatari | |
| 2004/0257575 A1 | 12/2004 | Yamaguchi et al. | |

FOREIGN PATENT DOCUMENTS

| | | |
|---|---|---|
| JP | 8-178897 A | 7/1996 |
| JP | 8-248266 A | 9/1996 |
| JP | 10-232210 A | 9/1998 |
| JP | 2000-2677 A | 1/2000 |
| JP | 2000-356746 | 12/2000 |
| JP | 2001-59829 A | 3/2001 |

OTHER PUBLICATIONS

Related U.S. Appl. No. 10/766,582, filed Jan. 27, 2004; Inventor: Jun Yamaguchi et al.; Title: Microchemical System, and Photothermal Conversion Spectroscopic Analysis Method Implemented by the System.

* cited by examiner

MICROCHEMICAL SYSTEM, AND PHOTOTHERMAL CONVERSION SPECTROSCOPIC ANALYSIS METHOD

This application is a Continuation Application under 35 U.S.C. 371 of International Application PCT/JP02/09464, filed Sep. 13, 2002.

THE NAMES OF THE PARTIES TO A JOINT RESEARCH AGREEMENT

1. Nippon Sheet Glass Co., Ltd., and
2. Kanagawa Academy of Science and Technology.

TECHNICAL FIELD

The present invention relates to a microchemical system, and a photothermal conversion spectroscopic analysis method.

BACKGROUND ART

In view of the rapidity of chemical reactions, and the need to carry out reactions using very small amounts of a sample, on-site analysis and so on, integration technology for carrying out chemical reactions in very small spaces has attracted attention from hitherto, and research has been carried out with vigor throughout the world.

So-called microchemical systems are one example of such integration technology. Microchemical systems are systems for carrying out mixing, reaction, separation, extraction, detection or the like on a sample solution (a liquid containing a sample) in a very fine channel formed in a small glass substrate or the like. Examples of reactions carried out in such a microchemical system include diazotization reactions, nitration reactions, and antigen-antibody reactions. Moreover, examples of extraction/separation include solvent extraction, electrophoretic separation, and column separation. A microchemical system may be used with a single function, for example for only separation, or may be used with a combination of a plurality of functions.

As an example of a microchemical system for only separation out of the above functions, an electrophoresis apparatus for analyzing extremely small amounts of proteins, nucleic acids or the like has been proposed (see, for example, Japanese Laid-open Patent Publication (Kokai) No. H8-178897). This electrophoresis apparatus has a channel-formed plate-shaped member comprised of two glass substrates joined together. Because the member is plate-shaped, breakage is less likely to occur than in the case of a glass capillary tube having a circular or rectangular cross section, and hence handling is easier.

In such a microchemical system, because the amount of the sample is very small, a highly sensitive detection method is essential. As such a method, a photothermal conversion spectroscopic analysis method that uses a thermal lens effect arising upon a sample solution in a very fine channel absorbing light has been established. This photothermal conversion spectroscopic analysis method uses a photothermal conversion effect in which light is convergently irradiated onto a sample solution, whereupon a solute in the sample solution absorbs the light and hence thermal energy is released, and thus the temperature of the solvent is locally raised by this thermal energy, whereby the refractive index of the sample solution changes, and hence a thermal lens is formed. This photothermal conversion spectroscopic analysis method has opened up a path for realizing microchemical systems.

Figure 3:
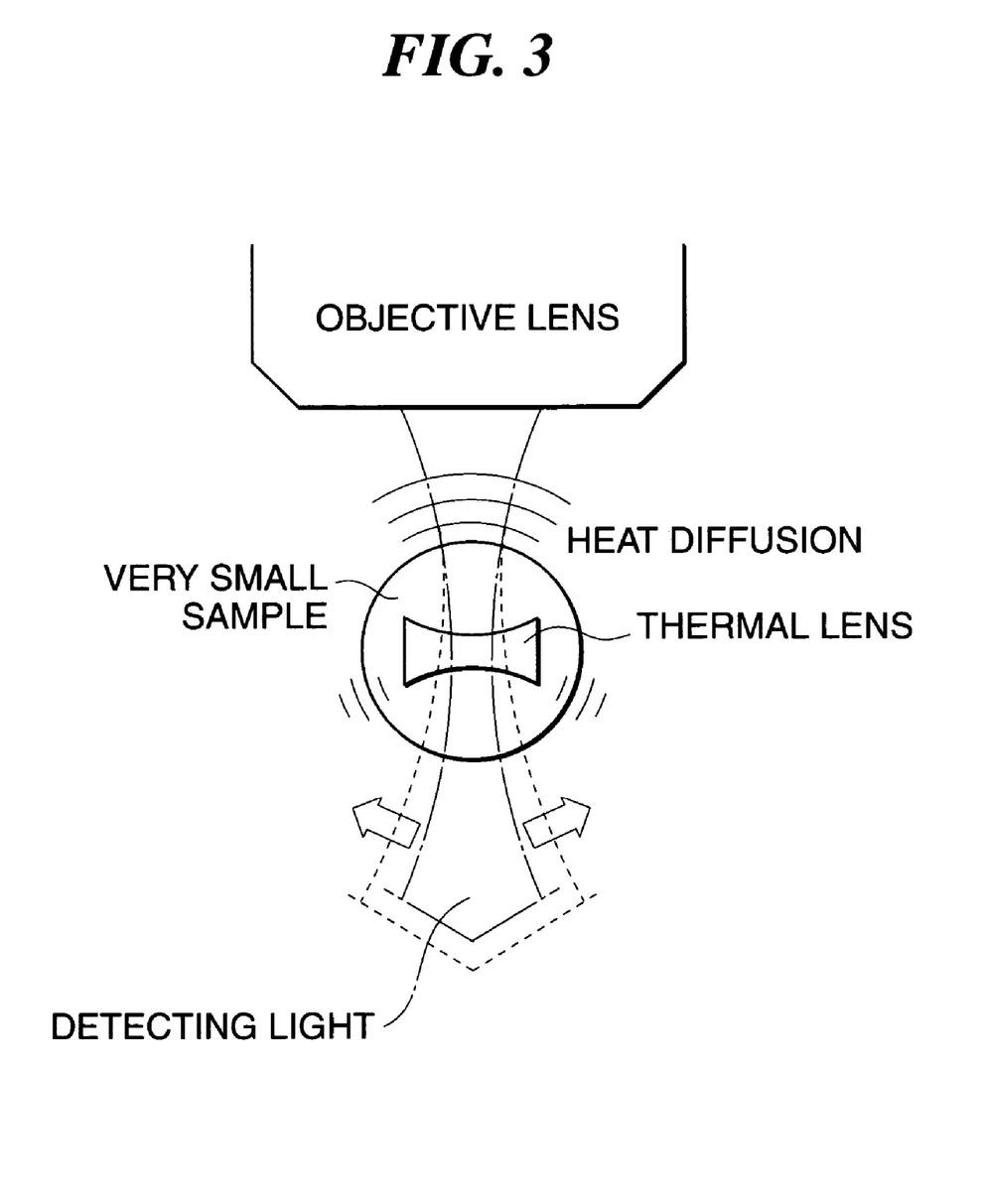
FIG. 3 is a view useful in explaining the principle of a thermal lens.

FIG. 3 is a view useful in explaining the principle of a thermal lens.

In FIG. 3, exciting light is convergently irradiated onto an extremely small amount of a sample solution via an objective lens of a microscope, whereby a photothermal conversion effect is brought about. For most substances, the refractive index drops as the temperature rises, and hence in the sample solution onto which the exciting light has been convergently irradiated, the refractive index drops, with the drop being larger the closer to the center of the converged light, which is where the rise in temperature is largest. In other words, it becomes such that the refractive index increases with distance from the center of the converged light. This is because the rise in temperature becomes smaller with distance from the center of the converged light due to thermal diffusion. Optically, the resulting refractive index distribution produces the same effect as a concave lens, and hence the effect is referred to as the thermal lens effect. The size of the thermal lens effect, i.e. the power of the concave lens, is proportional to the optical absorbance of the sample solution. Moreover, in the case that the refractive index increases with temperature, the change in the refractive index is reversed, and hence a thermal lens effect that produces the same effect as a convex lens arises.

In the photothermal conversion spectroscopic analysis method described above, changes in the refractive index of the sample solution due to thermal diffusion in the sample solution are thus observed, and hence the method is suitable for detecting the concentrations of extremely small samples.

An example of a photothermal conversion spectroscopic analysis apparatus that carries out the photothermal conversion spectroscopic analysis method described above is disclosed in Japanese Laid-open Patent Publication (Kokai) No. H10-232210.

In the conventional photothermal conversion spectroscopic analysis apparatus, a channel-formed plate-shaped member is disposed below the objective lens of a microscope, and exciting light of a predetermined wavelength outputted from an exciting light source is introduced into the microscope. The exciting light is thus convergently irradiated via the objective lens of the microscope onto a sample solution in the channel of the channel-formed plate-shaped member. The focal position of the convergently irradiated exciting light is made to be in the sample solution, and hence a thermal lens is formed centered on this focal position.

Moreover, detecting light having a wavelength different to that of the exciting light is outputted from a detecting light source, and is introduced into the microscope. The detecting light passes through and exits from the microscope, and is thus convergently irradiated onto the thermal lens that has been formed in the sample solution by the exciting light, and passes through the sample solution and is thus diverged (in the case that the thermal lens has the effect of a concave lens) or converged (in the case that the thermal lens has the effect of a convex lens). The diverged or converged detecting light exiting from the sample solution acts as signal light. The signal light passes through a converging lens and a filter, or just a filter, and is then received by a detector and thus detected. The intensity of the detected signal light depends on the refractive index of the thermal lens formed in the sample solution. Note also that alternatively the detecting light may have the same wavelength as the exciting light, or the exciting light may also be used as the detecting light.

In the photothermal conversion spectroscopic analysis apparatus, i.e. microchemical system, described above, a thermal lens is thus formed in the focal position of the exciting light, and changes in the refractive index of the thermal lens formed are detected using detecting light that has either the same wavelength as the exciting light or a different wavelength thereto.

However, with a photothermal conversion spectroscopic analysis apparatus as described above, the optical systems and so on for the light sources, the measurement section and the detection section (photoelectric conversion section) have a complex construction, and hence such an apparatus has been large in size, and has thus lacked portability. Consequently, there is a problem that there are limitations with regard to the installation space and the operation of the photothermal conversion spectroscopic analysis apparatus, and hence there is a problem of the work efficiency for a user being poor.

Moreover, in the photothermal conversion spectroscopic analysis apparatus, the exciting light and the detecting light are led to the sample solution through open space, and hence various optical system components such as the light sources, mirrors and lenses must be prevented from moving during measurement, and thus a sturdy baseplate for fixing these components is required. Furthermore, the optical axes of the exciting light and the detecting light may shift out of alignment upon changes in the environment such as changes in the temperature, and hence jigs for adjusting for such shifts are required. These jigs are also a cause of the photothermal conversion spectroscopic analysis apparatus becoming larger in size and hence lacking portability.

Figure 4A:
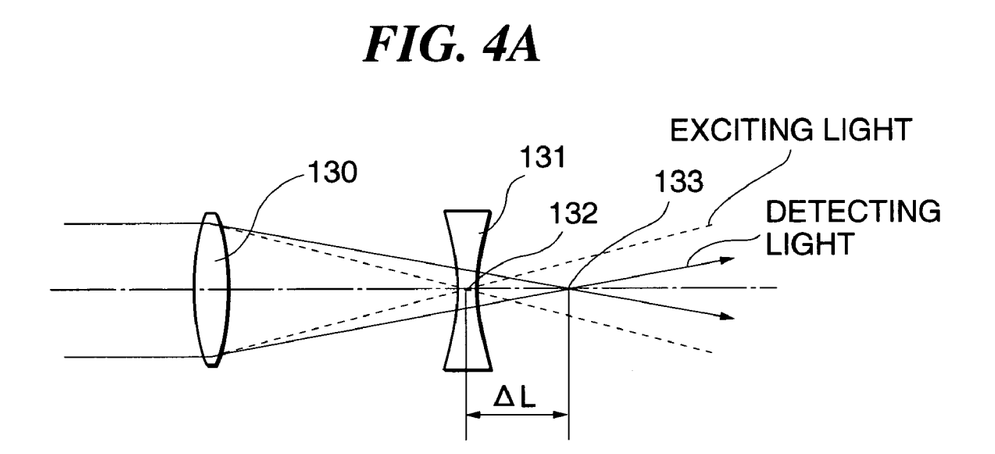
FIGS. 4A and 4B are views useful in explaining the formation position of a thermal lens and the focal position of detecting light in the direction of travel of exciting light; specifically.
Figure 4B:
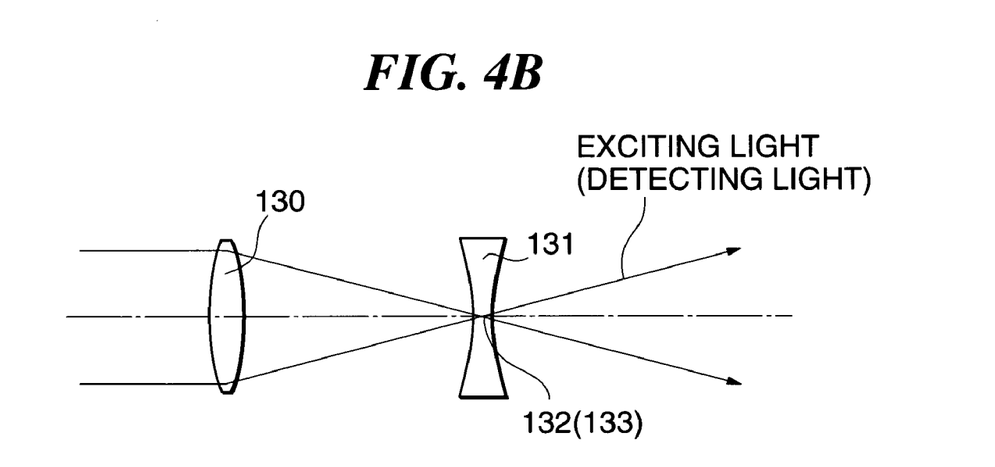

Moreover, in a microchemical system that uses the photothermal conversion spectroscopic analysis method, in many cases it is necessary for the focal position of the exciting light and the focal position of the detecting light to be different to one another. FIGS. 4A and 4B are views useful in explaining the formation position of a thermal lens and the focal position of detecting light in the direction of travel of exciting light; FIG. 4A shows a case in which an objective lens has chromatic aberration, and FIG. 4B shows a case in which the objective lens does not have chromatic aberration.

In the case that the objective lens 130 has chromatic aberration, as shown in FIG. 4A, the thermal lens 131 is formed at the focal position 132 of the exciting light, and the focal position 133 of the detecting light is in a position shifted by an amount $\Delta L$ from the focal position 132 of the exciting light; changes in the refractive index of the thermal lens 131 can thus be detected as changes in the focal distance of the detecting light. On the other hand, in the case that the objective lens 130 does not have chromatic aberration, as shown in FIG. 4B, the focal position 133 of the detecting light is almost exactly the same as the position of the thermal lens 131 formed at the focal position 132 of the exciting light. As a result, the detecting light is not refracted by the thermal lens 131, and hence changes in the refractive index of the thermal lens 131 cannot be detected.

Figure 5A:
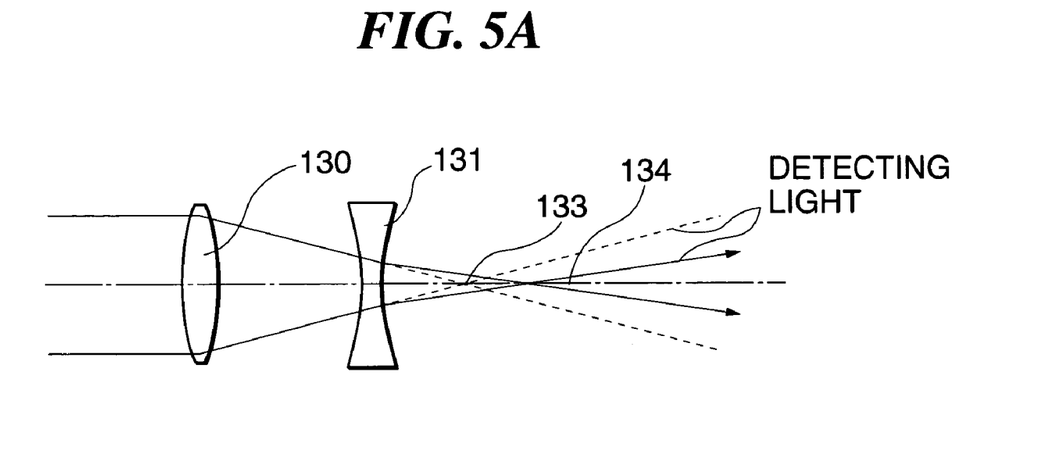
FIG. 5A shows a case in which the thermal lens is formed closer to the objective lens than is the focal position of the detecting light.
Figure 5B:
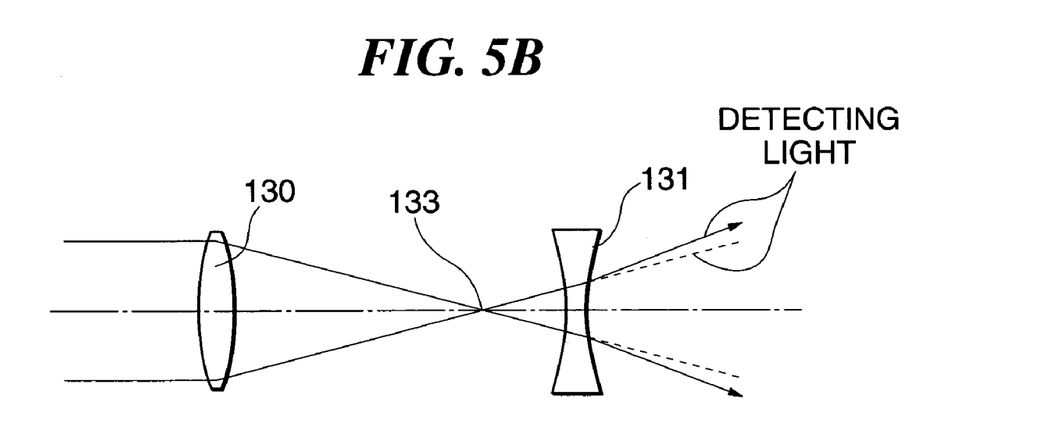
FIG. 5B shows a case in which the thermal lens is formed in a position further from the objective lens than is the focal position of the detecting light.
Figure 6:
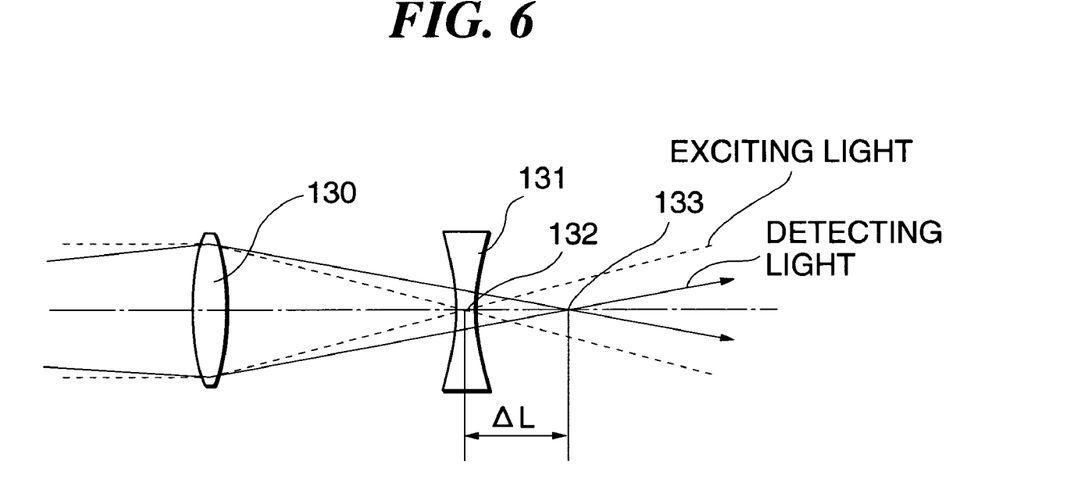
FIG. 6 is a view useful in explaining a method of detecting changes in refractive index of a thermal lens in a conventional photothermal conversion spectroscopic analysis apparatus, and shows a case in which a concave lens is put into an optical path so that detecting light is made into divergent light, and hence the focal position of the detecting light is made to be further away than the focal position of exciting light.

However, the objective lens of a microscope is generally manufactured so as not to have chromatic aberration, and hence for the reason described above, the focal position 133 of the detecting light is almost exactly the same as the position of the thermal lens 131 formed at the focal position of the exciting light (FIG. 4B). Changes in the refractive index of the thermal lens 131 thus cannot be detected. There is thus a problem that the position of the sample solution in which the thermal lens 131 is formed must be shifted from the focal position 133 of the detecting light every time measurement is carried out as shown in FIG. 5A or 5B, or else the detecting light must be diverged or converged slightly using a lens (not shown) before being introduced into the objective lens 130 so that the focal position 133 of the detecting light is shifted from the thermal lens 131 as shown in FIG. 6; consequently, the sensitivity of measurement may be degraded, and moreover the work efficiency for a user is poor.

It is an object of the present invention to provide a microchemical system, and a photothermal conversion spectroscopic analysis method carried out by the microchemical system, which are capable of carrying out measurement with high sensitivity, and moreover to provide a small-sized microchemical system which allows the work efficiency for a user to be improved.

DISCLOSURE OF THE INVENTION

To attain the above object, in a first aspect of the present invention, there is provided a microchemical system including an exciting light source that outputs exciting light, a detecting light source that outputs detecting light, a light-guiding optical system that combines and guides the exciting light and the detecting light, an irradiating lens for irradiating the exciting light and the detecting light guided by the light-guiding optical system onto a sample, detecting means for detecting the detecting light that has passed through a thermal lens formed through the sample being irradiated with the exciting light, and analyzing means for analyzing the sample based on the detected detecting light, wherein the microchemical system comprises a first light-introducing optical fiber that introduces the exciting light outputted from the exciting light source into the light-guiding optical system, a second light-introducing optical fiber that introduces the detecting light outputted from the detecting light source into the light-guiding optical system, a two-wavelength multiplexing device that is provided in the light-guiding optical system, for multiplexing the exciting light and the detecting light that have been introduced by the first light-introducing optical fiber and the second light-introducing optical fiber, and a light-guiding optical fiber that guides the multiplexed exciting light and detecting light to the irradiating lens, wherein the irradiating lens has chromatic aberration.

In the first aspect of the present invention, preferably, the two-wavelength multiplexing device has a multi-layer film that reflects or transmits light according to a wavelength of the light, wherein a wavelength of light at a borderline between light that is reflected and light that is transmitted by the multi-layer film lies between a wavelength of the exciting light and a wavelength of the detecting light.

In the first aspect of the present invention, preferably, the two-wavelength multiplexing device comprises two gradient index rod lenses connected together in series, and a dielectric multi-layer film filter, which is composed of the multi-layer film made of a dielectric, formed at bonding faces of the two gradient index rod lenses connected together.

In the first aspect of the present invention, preferably, the dielectric multi-layer film filter is formed on the gradient index rod lenses.

Preferably, the light-guiding optical fiber propagates the exciting light and the detecting light with a single mode.

In the first aspect of the present invention, preferably, the irradiating lens is fixed to an end of the light-guiding optical fiber from which the exciting light and the detecting light exit.

In the first aspect of the present invention, preferably, the exciting light and the detecting light have a different frequency to one another.

In the first aspect of the present invention, preferably, the irradiating lens is a gradient index lens.

In the first aspect of the present invention, preferably, the above gradient index lens is a cylindrical rod lens.

To attain the above object, in a second aspect of the present invention, there is provided a photothermal conversion spectroscopic analysis method comprising irradiating exciting light and detecting light onto a sample via an irradiating lens, and analyzing the sample by detecting the detecting light that has passed through a thermal lens formed through the sample being irradiated with the exciting light, wherein the exciting light and the detecting light are introduced, using a first light-introducing optical fiber and a second light-introducing optical fiber respectively, into a two-wavelength multiplexing device that multiplexes two types of light of different wavelengths, and the exciting light and the detecting light that have been multiplexed by the two-wavelength multiplexing device are guided to the irradiating lens using a light-guiding optical fiber with a single mode.

In the second aspect of the present invention, preferably, the two-wavelength multiplexing device multiplexes the exciting light and the detecting light by reflecting one of the exciting light and the detecting light and transmitting the other one of the exciting light and the detecting light using a dielectric multi-layer film filter formed between two gradient index rod lenses that are connected together in series.

BRIEF DESCRIPTION OF THE DRAWINGS

FIG. 4A shows a case in which an objective lens has chromatic aberration; and

FIG. 4B shows a case in which the objective lens does not have chromatic aberration;

FIGS. 5A and 5B are views useful in explaining the formation position of the thermal lens and the focal position of the detecting light in the direction of travel of the exciting light; specifically:

BEST MODE FOR CARRYING OUT THE INVENTION

Microchemical systems according to embodiments of the present invention will now be described in detail with reference to the drawings.

Figure 1:
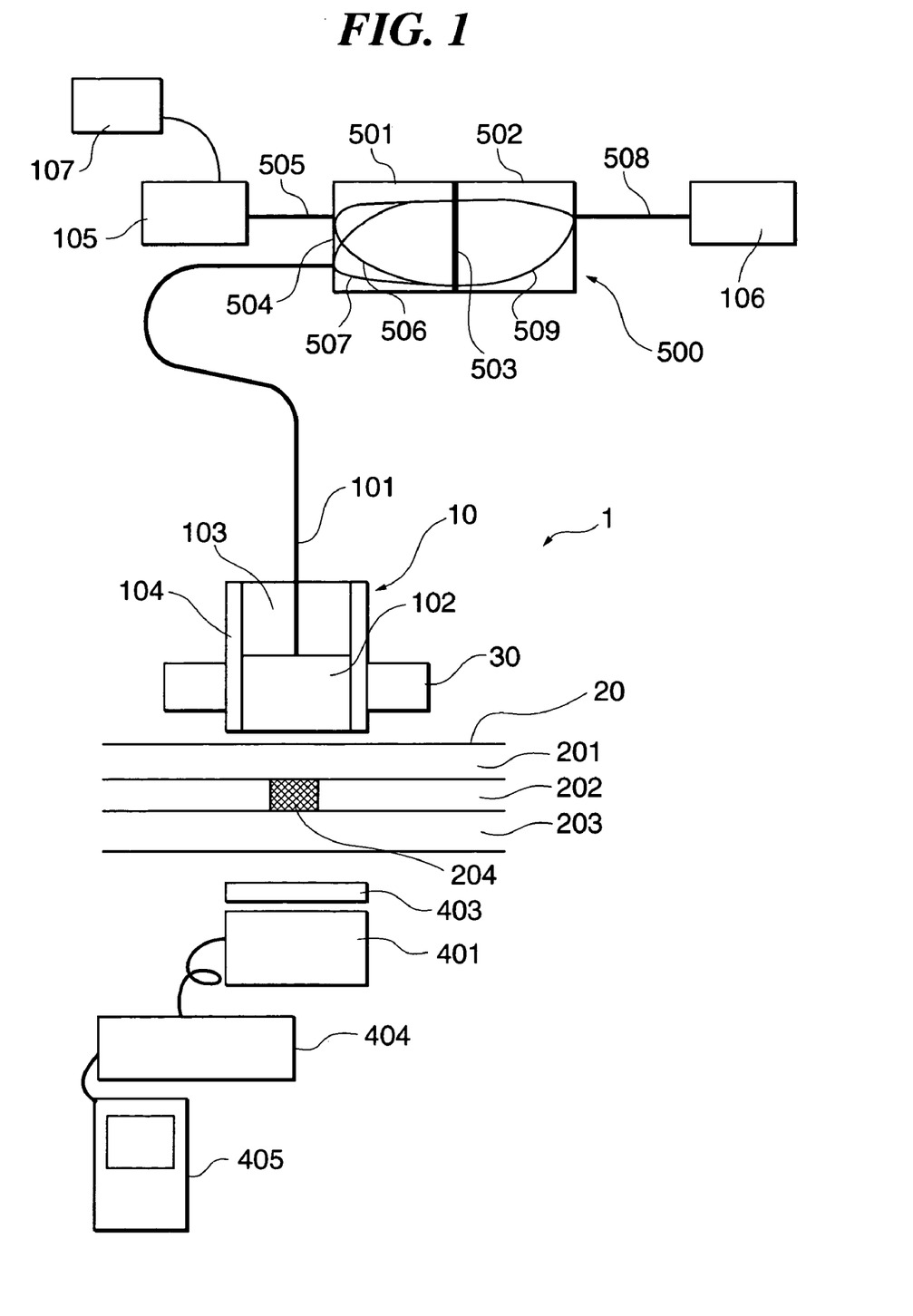
FIG. 1 is a view schematically showing the construction of a microchemical system according to a first embodiment of the present invention.

FIG. 1 is a view schematically showing the construction of a microchemical system according to a first embodiment of the present invention.

In FIG. 1, the microchemical system 1 has an optical fiber unit 10 having a lens built therein (hereinafter referred to as the "optical fiber unit 10"). The optical fiber unit 10 has a gradient index rod lens 102 as an objective lens inside a tube 104 at a front end thereof (the lower side in FIG. 1), and has an optical fiber 101 that propagates exciting light and detecting light with a single mode inserted in the tube 104 from a rear end thereof (the upper side in FIG. 1). The inserted end of the optical fiber 101 is connected to one end of the gradient index rod lens 102.

A ferrule 103 having an outside diameter the same as the outside diameter of the gradient index rod lens 102 is further built into the optical fiber unit 10 inside the tube 104 on the side of the above-mentioned end of the gradient index rod lens 102. The ferrule 103 is for making the outside diameter of the optical fiber 101 be the same as the outside diameter of the gradient index rod lens 102, and the optical fiber 101 is installed so as to pass through the ferrule 103. The optical fiber 101 is fixed in position by the ferrule 103, and the gradient index rod lens 102 and the ferrule 103 are fixed inside the tube 104. Here, the optical fiber 101 and the gradient index rod lens 102 may be in close contact with one another, or there may be a gap therebetween. The optical fiber unit 10 is fixed using a jig 30 in a position such that light exiting from the optical fiber unit 10 is perpendicularly incident on a channel-formed plate-shaped member 20, described below.

The gradient index rod lens 102 is a transparent cylindrical lens, and is configured such that the refractive index changes continuously in a radial direction from the position of a central axis thereof that extends in a longitudinal direction thereof. Such a rod lens is known as a converging light-transmitting body configured such that the refractive index $n(r)$ at a position a distance $r$ in the radial direction from the central axis is given approximately by the quadratic equation in $r$, $$n(r)=n_0\{1-(g^2/2)x\ r^2\},$$

wherein $n_0$ represents the refractive index at the central axis, and $g$ represents a quadratic distribution constant.

If the length $z_o$ of the gradient index rod lens 102 is chosen to be in a range of $0<z_0<\pi/2\ g$, then even though the gradient index rod lens 102 has flat end faces, the gradient index rod lens 102 will have the same image formation characteristics as an ordinary convex lens; when a parallel light beam is incident on the gradient index rod lens 102, a focal point will be formed at a position a distance $s_0$ from the end of the gradient index rod lens 102 from which the light beam exits, where $$s_0=cot(gz_0)/n_0g.$$

Such a gradient index rod lens 102 may be manufactured, for example, using the following method.

A glass rod having flat end faces is formed from a glass having as principal components thereof 57 to 63 mol % of $SiO_2$, 17 to 23 mol % of $B_2O_3$, 5 to 17 mol % of $Na_2O$, and 3 to 15 mol % of $Tl_2O$, and then the glass rod is treated in an ion exchange medium such as potassium nitrate, thus carrying out ion exchange between thallium ions and sodium ions in the glass and potassium ions in the ion exchange medium, and hence producing a refractive index distribution in the glass rod in which the refractive index decreases continuously from the center of the glass rod outward. A gradient index rod lens is thus manufactured.

Because the base of the gradient index rod lens 102 is flat, the end face of the optical fiber 101 can easily be installed, and moreover the optical axis of the gradient index rod lens 102 and the optical axis of the optical fiber 101 can easily be aligned with one another. Moreover, because the gradient index rod lens 102 is cylindrical, the optical fiber unit 10 can also easily be formed in a cylindrical shape. As a result, holding the optical fiber unit 10 using the jig 30 is extremely easy.

As the optical fiber 101, a single-mode optical fiber having only one propagation mode is used so that, when detecting a very small amount of a solute in a sample solution using the photothermal conversion spectroscopic analysis method, the exciting light will be narrowed down as much as possible, and hence the energy used in the photothermal conversion will be increased, and moreover the thermal lens produced by the exciting light will have little aberration.

The light exiting from the single-mode optical fiber 101 will always have a Gaussian distribution, and hence the focal point of the exciting light will be small in size. Moreover, in the case that the thermal lens produced by the exciting light is small in size, to make the amount of the detecting light that passes through the thermal lens be as high as possible, it is preferable to also narrow down the detecting light as much as possible. From this standpoint as well, it is preferable for the optical fiber to propagate the exciting light and the detecting light with a single mode.

Any type of optical fiber can be used as the optical fiber 101 insofar as it can transmit the exciting light and the detecting light. However, in the case that a multi-mode optical fiber is used, the exiting light will not have a Gaussian distribution, and moreover the pattern of the exiting light will vary according to various conditions such as the state of curvature of the optical fiber 101, and hence it will not necessarily be possible to obtain stable exiting light. Carrying out measurement on a very small amount of a solute will thus be difficult, and moreover there may be a lack of stability in the measured value. It is thus preferable for the optical fiber 101 to be a single-mode optical fiber as described above.

In the vicinity of an end of the optical fiber 101 opposite to the inserted end are provided an exciting light source 105 that outputs the exciting light for exciting the sample solution, a detecting light source 106 that outputs the detecting light that is irradiated onto the sample solution to detect information for carrying out analysis or the like on the sample solution, a modulator 107 for modulating the exciting light, and a two-wavelength multiplexing device 500 for multiplexing the exciting light and the detecting light to be introduced into the optical fiber 101.

The two-wavelength multiplexing device 500 has two gradient index rod lenses 501 and 502. The gradient index rod lenses 501 and 502 have approximately the same total length as one another. The gradient index rod lenses 501 and 502 are fixed together in series with one end face of each thereof placed together. An interference filter film 503, described below, is formed between these end faces. The exciting light source 105 is connected to one end face (hereinafter referred to as the "entering end face 504") of the gradient index rod lens 501 by an optical fiber 505. The optical fiber 505 is connected in a position offset from the center of the entering end face 504. One end of the optical fiber 101 is also connected to the entering end face 504. Moreover, the detecting light source 106 is connected to one end face of the gradient index rod lens 502 by an optical fiber 508. The optical fiber 508 is connected in a position offset from the center of this end face.

The gradient index rod lens 501 has a total length approximately ¼ of the meandering period of the light beam that enters off-axis. The interference filter film 503 is comprised of a dielectric multi-layer film, and is formed using a film formation method such as sputtering. The interference filter film 503 has a characteristic of reflecting the exciting light that has propagated through the optical fiber 505, but transmitting the detecting light that has propagated through the optical fiber 508.

With such a two-wavelength multiplexing device 500, the light beam exiting the optical fiber 505 from the exciting light that has propagated through the optical fiber 505 from the exciting light source 105 enters the gradient index rod lens 501 from the entering end face 504. This light beam becomes a light beam 506 which has its beam diameter increased while meandering through the gradient index rod lens 501, and the light beam 506 then strikes the interference filter film 503. The light beam 506 is reflected at the interference filter film 503, and then becomes a light beam 507, which enters the optical fiber 101.

On the other hand, the light beam exiting the optical fiber 508 from the detecting light that has propagated through the optical fiber 508 enters into the gradient index rod lens 502, and becomes a light beam 509 for which the beam diameter increases while meandering along, and then the light beam 509 strikes the interference filter film 503. The light beam 509 passes through the interference filter film 503, and then becomes the light beam 507 together with the exciting light, which enters the optical fiber 101.

As described above, the two-wavelength multiplexing device 500 is merely comprised of two gradient index rod lenses 501 and 502 fixed together with the interference filter film 503, which is a dielectric multi-layer film, therebetween; the number of component parts is thus low, and moreover all of the component parts can be fixed in place, and hence there is little loss of the exciting light and the detecting light in the two-wavelength multiplexing device 500, and there is stability to prolonged usage, whereby the measurement sensitivity and stability are improved. Moreover, the gradient index rod lenses 501 and 502 may be extremely small in size, and hence the two-wavelength multiplexing device will be extremely small in size, and thus the microchemical system can be made small in size.

The exciting light and detecting light that have been multiplexed by the two-wavelength multiplexing device 500 propagate through the optical fiber 101, enter the optical fiber unit 10, and exit from the gradient index rod lens 102. The light exiting from the gradient index rod lens 102 is perpendicularly incident on the channel-formed plate-shaped member 20. The channel-formed plate-shaped member 20 has therein a channel 204 through which a sample solution is passed, and is comprised of three glass substrates 201, 202 and 203 bonded on top of one another. The channel 204, through which the sample solution is passed when carrying out mixing, agitation, synthesis, separation, extraction, detection or the like, is formed in the glass substrate 202.

From the perspective of durability and chemical resistance, the material of the channel-formed plate-shaped member 20 is preferably a glass. In particular, considering usage with biological samples such as cell samples, for example in DNA analysis, a glass having high acid resistance and alkali resistance is preferable, specifically a borosilicate glass, a soda lime glass, an aluminoborosilicate glass, a quartz glass or the like. However, if the usage is limited accordingly, then a channel-formed plate-shaped member 20 manufactured using an organic material such as a plastic may be used instead.

Examples of adhesives that can be used to bond the glass substrates 201, 202 and 203 together include organic adhesives such as acrylic adhesives and epoxy adhesives, and inorganic adhesives; the adhesive may be, for example, an ultraviolet-curing type, a thermosetting type, or a two-liquid-curing type. Alternatively, the glass substrates 201, 202 and 203 may be fused together by heat fusion.

A photoelectric converter 401 for detecting the detecting light, and a wavelength filter 403 that separates the exciting light and the detecting light and selectively transmits only the detecting light, are provided in a position facing the optical fiber unit 10, with the channel-formed plate-shaped member 20 interposed therebetween. In order for only part of the detecting light to be selectively transmitted, a member having a pinhole formed therein may also be provided such that the pinhole is positioned in the optical path of the detecting light in a position upstream of the photoelectric converter 401. Signals obtained by the photoelectric converter 401 are sent to a lock-in amplifier 404 for carrying out synchronization with the modulator 107 used for modulating the exciting light, and are then analyzed by a computer 405.

According to the microchemical system 1 of the present embodiment, the two-wavelength multiplexing device 500 for multiplexing the exciting light and detecting light is comprised of two gradient index rod lenses 501 and 502 that are extremely small in size; as a result, the microchemical system can be made small in size. Moreover, the gradient index rod lens 102 is connected to the leading end of the optical fiber 101 that propagates the exciting light and the detecting light; as a result, there is no need to adjust the optical axes of the exciting light and the detecting light and the optical axis of the gradient index rod lens 102 each time measurement is carried out, and moreover jigs for aligning the optical axes and a sturdy baseplate are unnecessary, and hence the work efficiency of a user can be improved, and moreover the microchemical system can be made yet smaller in size.

The focal position of the exciting light that has exited from the gradient index rod lens 102 must be in the channel 204 of the channel-formed plate-shaped member 20. The gradient index rod lens 102 does not have to be in contact with the channel-formed plate-shaped member 20, but in the case that the gradient index rod lens 102 is made to be in contact with the channel-formed plate-shaped member 20, the focal position of the gradient index rod lens 102 can be adjusted through the thickness of the upper glass substrate 201 of the channel-formed plate-shaped member 20. In the case that the thickness of the upper glass substrate 201 is insufficient, a spacer for adjusting the focal position may be inserted between the gradient index rod lens 102 and the upper glass substrate 201. In the case that the focal position of the exciting light is fixed in advance to be in the channel 204 of the channel-formed plate-shaped member 20 in this way, subsequent adjustment of the focal position becomes unnecessary, and hence the microchemical system 1 can be made yet smaller in size.

The gradient index rod lens 102 is set such that the focal position of the detecting light is shifted slightly by an amount $\Delta L$ relative to the focal position of the exciting light (see FIG. 4A).

The confocal length Ic (nm) is given by $Ic=\pi \times (d/2)^2/\lambda_1$. Here, d represents the e Airy disk and is given by $d=1.22 \times \lambda_1/NA$, $\lambda_1$ represents the wavelength (nm) of the exciting light, and NA represents the numerical aperture of the gradient index rod lens 102. In the case of using an optical fiber, the numerical aperture of the light exiting from the optical fiber is small, and hence the numerical aperture of the optical fiber is used in the calculation of the confocal length when using a rod lens having a large numerical aperture.

The value $\Delta L$ varies according to the thickness of the sample on which measurements are to be carried out. When carrying out measurements on a sample having a thickness lower than the confocal length, it is most preferable for $\Delta L$ to be equal to $\sqrt{3} \times Ic$.

The value $\Delta L$ represents the difference between the focal position of the detecting light and the focal position of the exciting light, and hence the result is the same regardless of whether the focal distance of the detecting light is longer or shorter than the focal distance of the exciting light.

If the leading end of the optical fiber were processed into a spherical shape or the like to form a lens, then it would be possible to narrow down the exciting light and the detecting light without installing a separate lens at the leading end of the optical fiber. However, in this case, there would be hardly any chromatic aberration, and hence the focal positions of the exciting light and the detecting light would be almost the same as one another. There would thus be a problem of the thermal lens signal being hardly detectable. Moreover, other aberration would be high for the lens formed by processing the leading end of the optical fiber, and hence there would also be a problem of the focal points of the exciting light and the detecting light being large. In the present embodiment, a gradient index rod lens 102 is thus installed at the leading end of the optical fiber 101.

Figure 2:
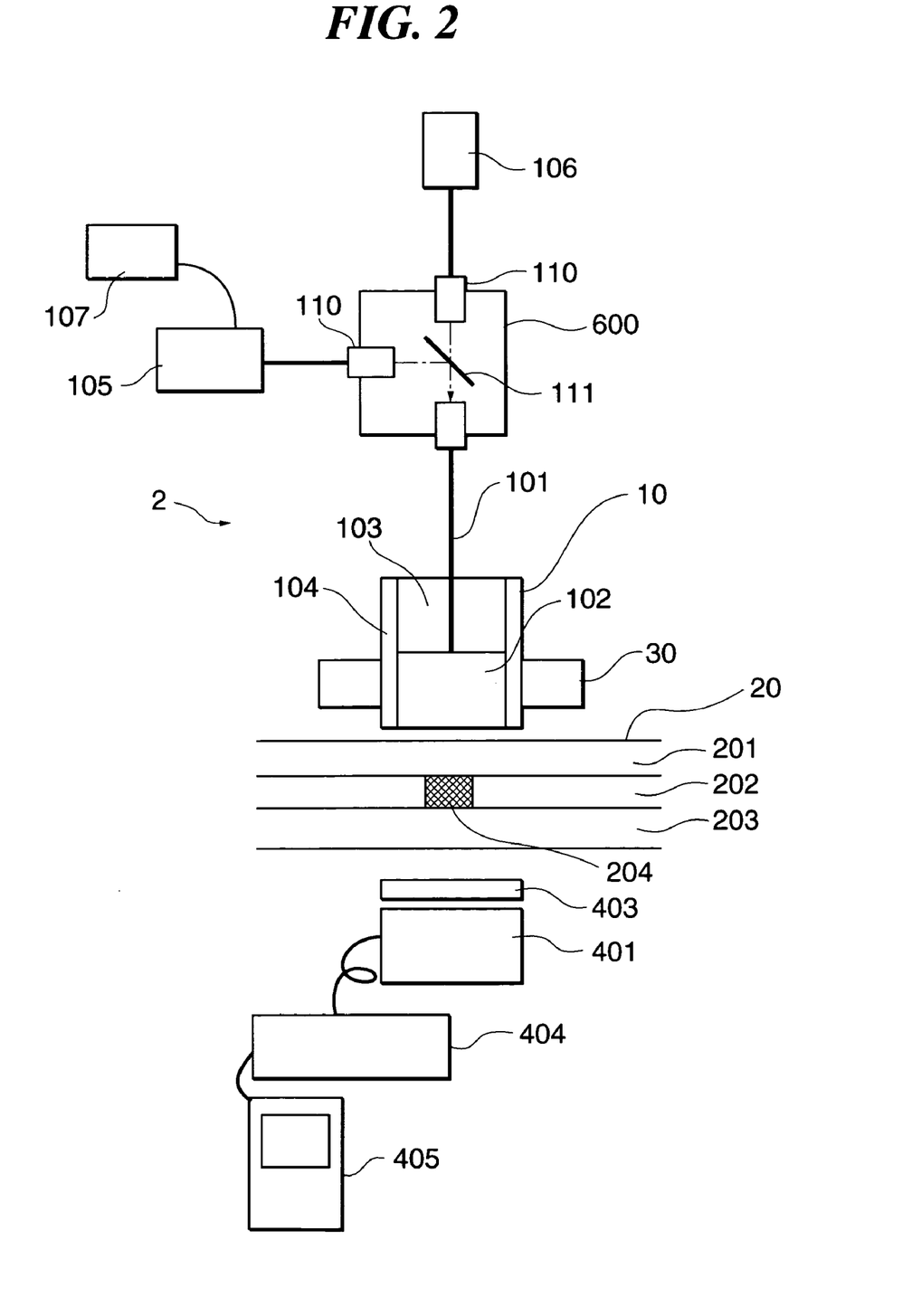
FIG. 2 is a view schematically showing the construction of a microchemical system according to a second embodiment of the present invention.

FIG. 2 is a view schematically showing the construction of a microchemical system according to a second embodiment of the present invention.

In FIG. 2, for the microchemical system 2 according to the second embodiment, component elements and parts corresponding to ones of the microchemical system 1 according to the first embodiment are represented by the same reference numerals as in the microchemical system 1 of the first embodiment, and description of these component elements and parts will be omitted here.

In the microchemical system 2 according to the present embodiment, a two-wavelength multiplexing device 600 differs from the two-wavelength multiplexing device 500 of the microchemical system 1 according to the first embodiment. The two-wavelength multiplexing device 600 does not have a construction like the two-wavelength multiplexing device 500 in which an interference filter film that is a dielectric multi-layer film is interposed between end faces of two gradient index rod lenses 501 and 502, but rather has a construction in which each of the exciting light and the detecting light propagates through an optical fiber and is then collimated using a collimator 110, and then the exciting light and the detecting light are multiplexed using a dielectric multi-layer film filter 111.

With the microchemical system 2 according to the present embodiment, the exciting light and the detecting light, which have each propagated through the optical fiber, are each collimated using the collimator 110, and are then multiplexed using the dielectric multi-layer film filter 111. The two-wavelength multiplexing device is thus slightly larger in size than in the microchemical system of the first embodiment. However, light that has been collimated is multiplexed, and hence alignment of the optical axes becomes easy, and thus a two-wavelength multiplexing device giving lower loss can easily be manufactured.

INDUSTRIAL APPLICABILITY

As described in detail above, according to the microchemical system of the present invention, the exciting light and the detecting light are introduced into the light-guiding optical system by the first light-introducing optical fiber and the second light-introducing optical fiber respectively. As a result, the exciting light and the detecting light can be introduced into the light-guiding optical system precisely. Moreover, the exciting light and the detecting light that have been introduced into the light-guiding optical system are multiplexed using the two-wavelength multiplexing device, and are then guided to the irradiating lens having chromatic aberration by the light-guiding optical fiber. As a result, the exciting light and the detecting light are always coaxial with one another. Moreover, there is no step in which the exciting light and the detecting light are led through open space, and hence there is no shifting of the optical axes due to changes in the environment such as changes in the temperature. Measurement can thus be carried out with high sensitivity. Furthermore, there is no need to adjust the optical axes of the exciting light and the detecting light, and hence the work efficiency of a user can be improved. Moreover, jigs and so on for adjusting the optical axes are unnecessary, and hence the microchemical system can be made smaller in size.

According to the microchemical system of the present invention, the exciting light and the detecting light are multiplexed using a two-wavelength multiplexing device having a multi-layer film that reflects or transmits light according to the wavelength of the light. As a result, the construction is simple and size reduction is easy, and hence the microchemical system can be made yet smaller in size.

According to the microchemical system of the present invention, the two-wavelength multiplexing device is comprised of two gradient index rod lenses connected together, and a dielectric multi-layer film filter formed therebetween that reflects one of the exciting light and the detecting light and transmits the other one of the exciting light and the detecting light. As a result, the two-wavelength multiplexing device becomes extremely small in size, and hence the microchemical system can be made yet smaller in size. Moreover, there is little loss of the exciting light and the detecting light in the two-wavelength multiplexing device, and there is stability to prolonged usage, and hence the measurement sensitivity and stability can be improved.

According to the microchemical system of the present invention, the dielectric multi-layer film filter is formed on the gradient index rod lenses. As a result, there is no need to combine the gradient index rod lenses with a dielectric multi-layer film filter that is separate to the gradient index rod lenses, and hence manufacture is easy. Moreover, a jig for combining the gradient index rod lenses and the dielectric multi-layer film filter is not necessary, and hence the microchemical system can be made yet smaller in size. Furthermore, there is a reduction in the number of surfaces that are involved in reflection, and hence there is a further reduction in loss of the exciting light and the detecting light, and hence the measurement sensitivity and stability can be further improved.

According to the microchemical system of the present invention, the optical fiber propagates the exciting light and the detecting light with a single mode. As a result, the thermal lens formed by the exciting light has little aberration, and hence more precise measurement can be carried out.

According to the microchemical system of the present invention, the exciting light and the detecting light have a different frequency to one another. As a result, the focal positions of the exciting light and the detecting light can be shifted from one another without adding any other optical systems. The microchemical system can thus be made yet smaller in size.

According to the microchemical system of the present invention, the exciting light and the detecting light have a different frequency to one another, and the irradiating lens has chromatic aberration. As a result, the focal positions of the exciting light and the detecting light can be shifted from one another without adding any other optical systems. The microchemical system can thus be made yet smaller in size.

According to the microchemical system of the present invention, the irradiating lens is a gradient index lens. As a result, the irradiating lens can be made small in size. The microchemical system can thus be made yet smaller in size.

According to the microchemical system of the present invention, the above gradient index lens is a cylindrical rod lens. As a result, the optical axis of the rod lens can easily be aligned with the optical axis of the light-guiding optical fiber, and moreover the rod lens can easily be held, and hence manufacture and maintenance are easy.

As described in detail above, according to a photothermal conversion spectroscopic analysis method of the present invention, exciting light and detecting light that have been multiplexed by a two-wavelength multiplexing device are propagated to an irradiating lens using a light-guiding optical fiber with a single mode. As a result, the exciting light and the detecting light are always coaxial with one another. Moreover, there is no step in which the exciting light and the detecting light are led through open space, and hence there is no shifting of the optical axes due to changes in the environment such as changes in the temperature. Measurement can thus be carried out with high sensitivity. Furthermore, there is no need to adjust the optical axes of the exciting light and the detecting light, and hence the work efficiency of a user can be improved.

According to the photothermal conversion spectroscopic analysis method of the present invention, the two-wavelength multiplexing device multiplexes the exciting light and the detecting light by reflecting one of the exciting light and the detecting light and transmitting the other one of the exciting light and the detecting light using a dielectric multi-layer film filter formed between two gradient index rod lenses that are connected together. As a result, there is little loss of the exciting light and the detecting light in the two-wavelength multiplexing device, and the exciting light and the detecting light are stable to prolonged usage. The measurement sensitivity and stability can thus be improved.

The invention claimed is:
1. A microchemical system comprising:
an exciting light source that outputs exciting light;
a detecting light source that outputs detecting light;
a light-guiding optical system that combines and guides the exciting light and the detecting light;
an irradiating lens for irradiating the exciting light and the detecting light guided by said light-guiding optical system onto a sample;

detecting means for detecting the detecting light that has passed through a thermal lens formed due to the sample being irradiated with the exciting light;

analyzing means for analyzing the sample based on the detected detecting light;

a first light-introducing optical fiber that introduces the exciting light outputted from said exciting light source into said light-guiding optical system;

a second light-introducing optical fiber that introduces the detecting light outputted from said detecting light source into said light-guiding optical system;

a two-wavelength multiplexing device which is provided in said light-guiding optical system, and which multiplexes the exciting light and the detecting light that have been introduced by said first light-introducing optical fiber and said second light-introducing optical fiber; and a light-guiding optical fiber that guides the multiplexed exciting light and detecting light to said irradiating lens;

wherein said irradiating lens has chromatic aberration.

2. A microchemical system as claimed in claim 1, wherein said two-wavelength multiplexing device includes a multi-layer film that reflects or transmits light according to a wavelength of the light, wherein a wavelength of light at a borderline between light that is reflected and light that is transmitted by said multi-layer film lies between a wavelength of the exciting light and a wavelength of the detecting light.

3. A microchemical system as claimed in claim 2, wherein said two-wavelength multiplexing device comprises two gradient index rod lenses connected together in series, and said multi-layer film comprises a dielectric multi-layer film filter which formed at faces of said two gradient index rod lenses that are connected together.

4. A microchemical system as claimed in claim 3, wherein said dielectric multi-layer film filter is formed on said gradient index rod lenses.

5. A microchemical system as claimed in claim 1, wherein said light-guiding optical fiber propagates the exciting light and the detecting light with a single mode.

6. A microchemical system as claimed in claim 1, wherein said irradiating lens is fixed to an end of said light-guiding optical fiber from which the exciting light and the detecting light exit.

7. A microchemical system as claimed in claim 1, wherein the exciting light and the detecting light have respective different frequencies.

8. A microchemical system as claimed in claim 1, wherein said irradiating lens is a gradient index lens.

9. A microchemical system as claimed in claim 8, wherein said gradient index lens is a cylindrical rod lens.

10. A photothermal conversion spectroscopic analysis method comprising:

irradiating exciting light and detecting light onto a sample via an irradiating lens; and analyzing the sample by detecting the detecting light that has passed through a thermal lens formed due to the sample being irradiated with the exciting light;

wherein the irradiating of the exciting light and the detecting light onto the sample comprises introducing the exciting light and the detecting light, through a first light-introducing optical fiber and a second light-introducing optical fiber, respectively, into a two-wavelength multiplexing device that multiplexes the exciting light and the detecting light, and guiding the exciting light and the detecting light that have been multiplexed by the two-wavelength multiplexing device to the irradiating lens through a light-guiding optical fiber with a single mode; and wherein the two-wavelength multiplexing device multiplexes the exciting light and the detecting light by reflecting a first one of the exciting light and the detecting light and transmitting a second one of the exciting light and the detecting light using a dielectric multi-layer film filter formed between two gradient index rod lenses that are connected together in series.

* * * * *